(12) United States Patent
Kaiser et al.

(10) Patent No.: US 9,403,053 B2
(45) Date of Patent: Aug. 2, 2016

(54) EXERCISE PROMOTION, MEASUREMENT, AND MONITORING SYSTEM

(75) Inventors: William J. Kaiser, Los Angeles, CA (US); Lawrence Au, Los Angeles, CA (US); Maxim A. Batalin, San Diego, CA (US); Alexander A. Bui, Los Angeles, CA (US); Bruce H. Dobkin, Los Angeles, CA (US); Xiaoyu Xu, Los Angeles, CA (US); Brett Jordan, Los Angeles, CA (US); Seth Thomas, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 135 days.

(21) Appl. No.: 14/122,639

(22) PCT Filed: May 25, 2012

(86) PCT No.: PCT/US2012/039714
§ 371 (c)(1),
(2), (4) Date: Feb. 20, 2014

(87) PCT Pub. No.: WO2012/162667
PCT Pub. Date: Nov. 29, 2012

(65) Prior Publication Data
US 2014/0256512 A1  Sep. 11, 2014

Related U.S. Application Data

(60) Provisional application No. 61/490,529, filed on May 26, 2011.

(51) Int. Cl.
*A63B 24/00*  (2006.01)
*A63B 22/06*  (2006.01)
(Continued)

(52) U.S. Cl.
CPC ........... *A63B 22/0605* (2013.01); *A63B 21/015* (2013.01); *A63B 22/0007* (2013.01);
(Continued)

(58) Field of Classification Search
CPC ........... A63B 22/0605; A63B 22/0694; A63B 22/0007; A63B 2220/34; A63B 2220/54; A63B 2220/89; A63B 21/00069; A63B 21/015; A63B 2225/50; A63B 71/0622; A63B 24/00; A63B 24/0062
See application file for complete search history.

(56) References Cited

U.S. PATENT DOCUMENTS 5,027,303 A * 6/1991 Witte .................... A61B 5/222
  482/8
5,459,329 A   10/1995 Sinclair
(Continued)

FOREIGN PATENT DOCUMENTS

GB       2351554 A    1/2003
WO    WO 0078413 A1 * 12/2000 ......... A63B 71/0622

OTHER PUBLICATIONS

Johnson M K et al, Retrographic sensing for the measurement of surface texture and shape, 2009 IEEE Conference on Computer Vision and Pattern Recognition, Miami Beach Florida USA, Jun. 20, 2009, pp. 1070-1077, XP03607061, ISBN: 978-1-4244-3992-8.

(Continued)

*Primary Examiner* — Glenn Richman
(74) *Attorney, Agent, or Firm* — Haverstock and Owens LLP

(57) ABSTRACT

An exercise system comprising: an exercise cycle comprising a crank, wherein the crank is configured to be rotated by a user; and a sensing unit coupled to the exercise cycle, wherein the sensing unit is configured to sense information related to at least one crank measurement and to transmit the information related to the at least one crank measurement to a remote device via wireless communication. In some embodiments, the remote device is a mobile device. In some embodiments, the at least one crank measurement comprises a rotational speed of the crank or a force applied to the crank. The remote device can display information related to use of the exercise cycle based on the information received from the exercise cycle.

19 Claims, 5 Drawing Sheets

(51) Int. Cl.
    *A63B 71/06*     (2006.01)
    *A63B 21/015*     (2006.01)
    *A63B 22/00*     (2006.01)
    *G06F 19/00*     (2011.01)
    *G06Q 50/22*     (2012.01)
    *A63B 21/00*     (2006.01)

(52) U.S. Cl.
    CPC ......... *A63B22/0694* (2013.01); *A63B 24/0062* (2013.01); *A63B 71/0622* (2013.01); *G06F 19/3481* (2013.01); *G06Q 50/22* (2013.01); *A63B 21/00069* (2013.01); *A63B 2024/0065* (2013.01); *A63B 2071/065* (2013.01); *A63B 2220/34* (2013.01); *A63B 2220/54* (2013.01); *A63B 2220/89* (2013.01); *A63B 2225/20* (2013.01); *A63B 2225/50* (2013.01); *A63B 2230/75* (2013.01)

(56) References Cited

U.S. PATENT DOCUMENTS

| | | | |
|---|---|---|---|
| 7,557,731 B2 * | 7/2009 | Ramasubbu | G08G 1/095 340/572.4 |
| 2006/0022833 A1 | 2/2006 | Ferguson et al. | |
| 2008/0191864 A1 | 8/2008 | Wolfson | |
| 2008/0225041 A1 | 9/2008 | El Dokor et al. | |
| 2008/0318679 A1 | 12/2008 | Tran et al. | |
| 2009/0189874 A1 | 7/2009 | Chene et al. | |
| 2010/0035688 A1 | 2/2010 | Picunko | |
| 2010/0152619 A1 | 6/2010 | Kalpaxis et al. | |
| 2010/0222711 A1 | 9/2010 | Lajeunesse | |
| 2010/0245245 A1 | 9/2010 | Yamada et al. | |
| 2011/0304541 A1 | 12/2011 | Dalal | |
| 2011/0306397 A1 | 12/2011 | Fleming et al. | |

OTHER PUBLICATIONS

Nagata K et al, Feature detection with an image based compliant tactile sensor, Proceedings of the 1999 IEEE/RSJ International Conference on Intelligent Robots and Systems. (IROS'99). Human and Environmental Friendly Robots With Intelligence and Emotional Quotients, Kyongju, Korea Oct. 17, 1999, pp. 838-843, XP002175226, ISBN 978-0-783-5185-1.

* cited by examiner

EXERCISE PROMOTION, MEASUREMENT, AND MONITORING SYSTEM

CROSS-REFERENCE TO RELATED APPLICATIONS

This application claims priority to U.S. Provisional Application Ser. No. 61/490,529, filed May 26, 2011, entitled "EXERCISE PROMOTION, MEASUREMENT, AND MONITORING SYSTEM," which is hereby incorporated by reference in its entirety as if set forth herein.

FIELD OF THE INVENTION

The present invention relates to a system and method of exercise promotion, measurement, and monitoring.

BACKGROUND OF THE INVENTION

Physical rehabilitation has become increasingly important for subjects recovering from treatment in clinics and from disease conditions including stroke. A particularly critical requirement is the support of individuals who suffer from impaired mobility or who may be confined to beds, yet must be provided with an assured fitness promotion regimen.

Stroke is a prominent cause of long-term disability in the United States. According to the American Heart Association (AHA), 800,000 people experience strokes every year. Stroke patients often lose essential sensorimotor skills. Consequently, the main objective of stroke rehabilitation is to re-enable patients' functional skills so they will be able to perform daily tasks. Physical activity, coupled with a regimented program, has been shown to reduce the probability of future strokes and prevent major loss of functional skills. Aerobic exercise has been shown to provide benefits for chronic stroke patients through intervention in both upper and lower extremities, even when the subjects were exercising while sitting. Unfortunately, many stroke survivors suffer from physical deconditioning, which further leads to cardiovascular risk factors and problems. As a result, an immediate solution is needed for stroke patients during rehabilitation. Specifically, physicians need to engage patients in repetitive exercises. With the increasingly prohibitive cost of hospital stay and pressure to discharge patients as soon as possible, a cost-effective solution to stroke rehabilitation is crucial.

Conventional low cost exercise cycle devices provide a means for enabling patient exercise. However, these devices are limited since they do not report energy expenditure that is critical to establishing whether a subject user is meeting a prescribed exercise regimen or has improved or declined. The lack of knowledge of actual workload may result in inadequate or excessive exercise. Conventional low cost exercise cycle devices also do not include the capability for local guidance and remote monitoring. Without these capabilities, it is not possible for a caregiver or healthcare enterprise to monitor all patients to ensure adherence to an exercise protocol.

An urgent need exists for low cost, rapidly deployable systems that enable exercise activity for patients in the clinic, those recovering in the community, the frail elderly, and those disabled.

SUMMARY OF THE INVENTION

The present invention provides a sensor-equipped portable exercise cycle that continuously measures arm and leg cycling activities through a mobile device in real time. Preferably, both cadence and torque, two important parameters for evaluating progress of rehabilitation, can be measured and logged continuously via a wireless interface. Sensor data are stored and relayed to a remote server. This system enables a dramatic cost reduction and increased deployment capability.

In one aspect of the present invention, an exercise system comprises: an exercise cycle comprising a crank, wherein the crank is configured to be rotated by a user; and a sensing unit coupled to the exercise cycle, wherein the sensing unit is configured to sense information related to at least one crank measurement and to transmit the information related to the at least one crank measurement to a remote device via wireless communication.

In some embodiments, the at least one crank measurement comprises a rotational speed of the crank or a force applied to the crank. In some embodiments, the remote device is configured to determine the at least one crank measurement using the transmitted information.

In some embodiments, the exercise cycle further comprises a resistance hub, and the crank comprises a first arm and a second arm, the first arm extending from a first side of the resistance hub and terminating in a first end, and the second arm extending from a second side of the resistance hub opposite the first side and terminating in a second end. In some embodiments, a first pedal is coupled to the first arm at the first end, and a second pedal is coupled to the second arm at the second end.

In some embodiments, the at least one crank measurement comprises a rotational speed of the crank. In some embodiments, the sensing unit is configured to register a trigger event when the crank passes a sampling location. In some embodiments, the sensing unit is configured to measure the rotational speed of the crank by measuring the time between successive trigger events or to register the trigger event with a remote device that is configured to measure the rotational speed of the crank by measuring the time between successive trigger events. In some embodiments, a magnet is coupled to the crank, wherein the magnet produces a magnetic field having a magnitude, and the sensing unit is configured to detect the magnetic field and to produce a voltage that is proportional to the magnitude of the magnetic field. In some embodiments, the sensing unit comprises a Hall-effect sensor. In some embodiments, the sensing unit is configured to measure the rotational speed of the crank by measuring the time between successive voltage peaks or to communicate the produced voltage to a remote device that is configured to measure the rotational speed of the crank by measuring the time between successive voltage peaks.

In some embodiments, the at least one crank measurement comprises the force applied to the crank. In some embodiments, the sensing unit is configured to measure torque of the crank using the applied force measurement or to communicate the applied force to a remote device that is configured to measure torque of the crank using the applied force measurement.

In some embodiments, the exercise cycle further comprises a resistance hub and a tab coupled to the resistance hub, wherein the crank is configured to translate the force that is applied to it to the tab, and the tab is configured to apply the force that is applied to it to the sensing unit. In some embodiments, the sensing unit comprises a polymer force sensor. In some embodiments, the sensing unit comprises a polymer conductive strain sensor.

In some embodiments, the sensing unit is configured to be used to determine the rotational speed of the crank and the force applied to the crank. In some embodiments, the sensing unit is configured to determine the rotational speed of the crank or to transmit information related to the rotational speed of the crank to a remote device that is configured to determine the rotational speed of the crank using the transmitted information related to the rotational speed of the crank, and the sensing unit is configured to determine the torque of the crank or to transmit information related to the force applied to the crank to a remote device that is configured to determine the torque of the crank using the transmitted information related to the force applied to the crank.

In some embodiments, the exercise cycle further comprises a resistance hub and a resistance control knob coupled to the resistance hub, wherein the resistance control knob is configured to control an amount of resistance to movement of the crank. In some embodiments, the exercise system further comprises plastic friction pads configured to sandwich a portion of the crank with a clamping force, wherein the resistance control knob is configured to adjust the clamping force.

In another aspect of the present invention, a method of monitoring exercise comprises: receiving, by a remote device, information transmitted from an exercise cycle comprising a crank, wherein the information is related to at least one crank measurement; and displaying, by the remote device, information related to use of the exercise cycle based on the information received from the exercise cycle.

In some embodiments, the information related to use of the exercise cycle comprises cadence. In some embodiments, the information related to use of the exercise cycle comprises torque. In some embodiments, the information related to use of the exercise cycle comprises a user's performance on the exercise cycle in relation to a desired measurement.

In yet another aspect of the present invention, a program storage device readable by a machine, tangibly embodying a program of instructions executable by the machine to perform a method of monitoring exercise is provided. The method comprises: receiving information related to at least one crank measurement of an exercise cycle; and displaying information related to use of the exercise cycle based on the received information.

In some embodiments, the information related to use of the exercise cycle comprises cadence. In some embodiments, the information related to use of the exercise cycle comprises torque. In some embodiments, the information related to use of the exercise cycle comprises a user's performance on the exercise cycle in relation to a desired measurement.

DETAILED DESCRIPTION OF THE INVENTION

The following description is presented to enable one of ordinary skill in the art to make and use the invention and is provided in the context of a patent application and its requirements. Various modifications to the described embodiments will be readily apparent to those skilled in the art and the generic principles herein can be applied to other embodiments. Thus, the present invention is not intended to be limited to the embodiment shown but is to be accorded the widest scope consistent with the principles and features described herein.

The present invention can be provided as a computer program product that can include a machine-readable medium having stored thereon instructions that can be used to program a computer (or other electronic devices) to perform a process according to the present invention. The machine-readable medium can include, but is not limited to, floppy diskettes, optical disks, CD-ROMs, ROMs, RAMs, magnet or optical cards, or other type of media/machine-readable medium suitable for storing electronic instructions.

Furthermore, it is contemplated that any features from any embodiment can be combined with any features from any other embodiment. In this fashion, hybrid configurations of the disclosed embodiments are well within the scope of the present invention.

Various aspects of the disclosure can be described through the use of flowcharts. Often, a single instance of an aspect of the present disclosure can be shown. As is appreciated by those of ordinary skill in the art, however, the protocols, processes, and procedures described herein can be repeated continuously or as often as necessary to satisfy the needs described herein. Additionally, it is contemplated that method steps can be performed in a different order than the order illustrated in the figures, unless otherwise disclosed explicitly or implicitly.

The present invention provides an exercise system that, in some embodiments, monitors applied force, generated power, and dissipated energy. This data is provided as guidance in real time, as well being archived, processed, and made available to service providers that, in turn, guide patients in a local or remote environment and ensure adherence to a prescribed exercise regimen. Clinical trials of the present invention have shown the benefits of exercise for treatment of many diverse conditions ranging from stroke, to respiratory disorders, to geriatric subjects with multiple diagnoses. Trial results of the present invention also show a reduction in length of hospital stay resulting from promotion of patient exercise. Guidelines have also been developed for rehabilitative exercise.

Figure 1:
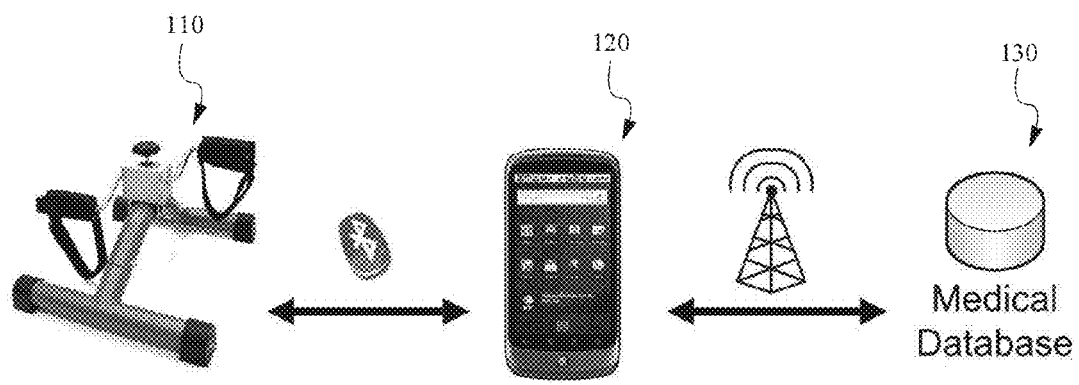
FIG. 1 illustrates an architecture for an exercise promotion, measurement, and monitoring system in accordance with some embodiments of the present invention.

FIG. 1 illustrates an architecture for an exercise promotion, measurement, and monitoring system in accordance with some embodiments of the present invention. The present invention provides a compact exercise cycle 110, which is preferably capable of sensing both cadence (i.e., speed of rotation) and torque generated by subjects for quantitative analyses. In some embodiments, sensor systems are integrated into the mechanical structure of the exercise cycle 110, minimizing potential hindrance to patients. The present invention takes into consideration the need of caregivers and users for detailed sensor data, and real-time feedback to system users. Preferably, sensor data generated by the exercise cycle 110 is transmitted to a local mobile device 120 and to a remote host 130, such as a host that comprises a medical database, via the mobile device 120. In some embodiments, the sensor data is transmitted directly to the remote host 130. Preferably, feedback to patients is provided by real-time computation of sensor system parameters. The present invention leverages low-cost sensor technology specifically selected to reduce the cost of microelectronic interfaces. It is important to note that its use is widely applicable to many exercise applications for healthy subjects or patient treatment.

In some embodiments, the sensing and local area wireless communication employed by the present invention exploits low power local area networking choices. In some embodiments, Bluetooth technology is employed since it enables convenient access to widely available mobile devices. In some embodiments, this wireless communication is implemented in the exercise cycle of the present invention with the MicroLEAP compact sensing platform (L. Au, W. Wu, M. Batalin, D. McIntire, and W. Kaiser, "MicroLEAP: Energy-aware Wireless Sensor Platform for Biomedical Sensing Applications," in *Biomedical Circuits and Systems Conference, 2007. BIOCAS 2007.IEEE*, November 2007, pp. 158-162). MicroLEAP enables real-time energy accounting and management. In some embodiments, it is configured to be placed in low-power modes to conserve battery life, based on real-time application needs. An 8-channel, 16-bit ADC is available for incorporating custom analog sensors in the exercise cycle of the present invention. MicroLEAP supports both an Li-Polymer battery and an AC wall adapter. With continuous wireless data transfer, it can operate for over 24 hours with a fully charged battery. In some embodiments, the Bluetooth interface is controlled through an ASCII-based protocol via Serial Port Profile (SPP). Basic operations, such as selecting sampling frequency and sensor channels, can be accomplished in user-level applications.

In some embodiments, acquiring sensor data from MicroLEAP can be completed with any Bluetooth-enabled mobile device that supports SPP. In some embodiments, sensor data are collected using an Android-based mobile device. In some embodiments, a graphical user interface (GUI) is designed for both data collection and real-time data display. In some embodiments, sensor data in Android, or some other operating system, are logged in successive data files and transmitted to a remote data center through Wi-Fi (802.11) connections or via cellular data or via wireline interfaces. Although reference is made above to specific operating systems and wireless communication technologies, it is contemplated that other operating systems and wireless communication technologies are within the scope of the present invention.

Figure 2A:
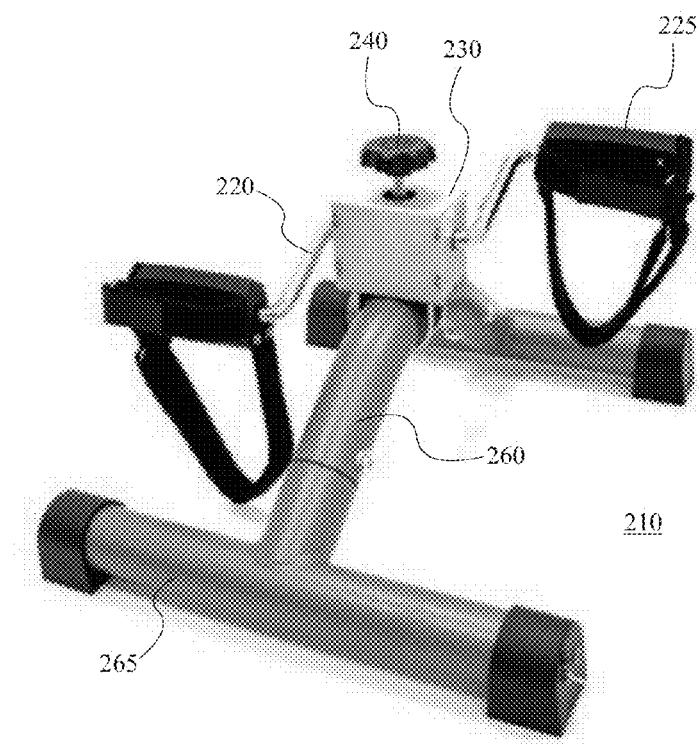
FIG. 2A illustrates a perspective view of an exercise cycle in accordance with some embodiments of the present invention.
Figure 2B:
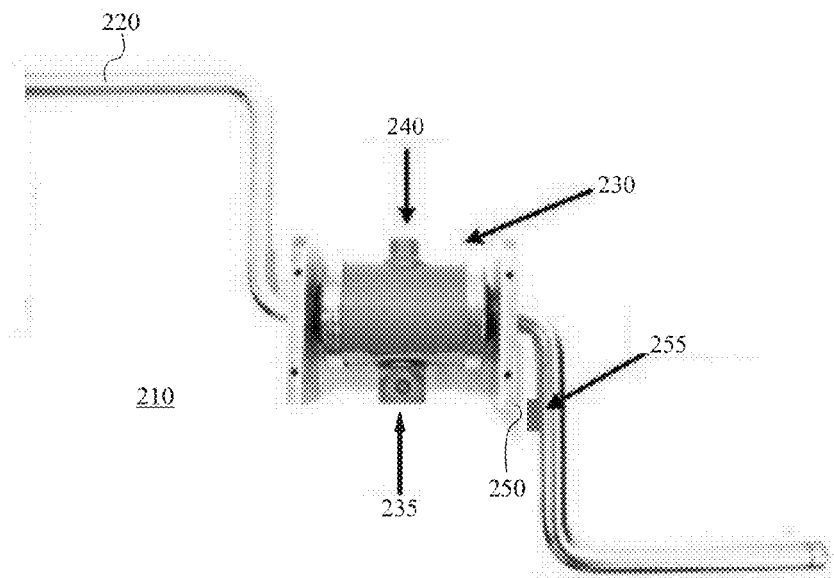
FIG. 2B illustrates a front view of an exercise cycle in accordance with some embodiments of the present invention.
Figure 2C:
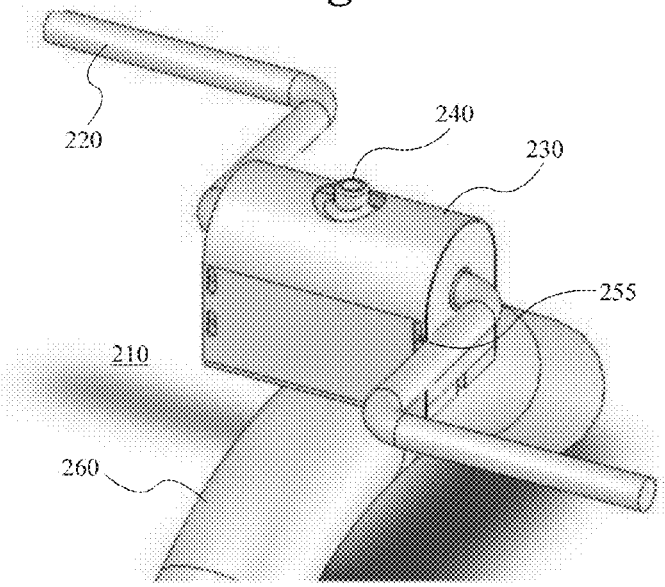
FIG. 2C illustrates another perspective view of an exercise cycle in accordance with some embodiments of the present invention.

FIG. 2A-C illustrate the major components of an exercise cycle 210 of the present invention. The exercise cycle 210 comprises a crank 220 that is configured to be rotated by a subject user with hands or feet. In some embodiments, the crank 220 comprises pedals 225 on opposite sides of the crank 220 in order to aid the user in rotating the crank 220. Preferably, the crank 220 is a one-piece crank. In some embodiments, force exerted on the crank 220 is translated to a customized welded tab 235 underneath a floating resistance control hub 230 on the exercise cycle 210. The resistance control hub 230 is configured to control pedaling resistance (i.e., resistance to crank rotation). In some embodiments, the required pedaling force can be controlled by adjusting a resistance knob 240 on the top of the hub 230, which increases the clamping force on two plastic friction pads that sandwich the middle portion of the crank 220.

In some embodiments, the exercise cycle 210 acquires both force and rotational data through its sensing interface, and relays them to a mobile device (e.g., mobile device 120) via wireless communication, (e.g., the Bluetooth interface). The caregiver or patient user can decide if real-time display is necessary or if the sensor data should be archived and transferred to a remote location (e.g., remote host 130) for future analyses in support of guidance. Guidance information can then range from real time feedback based on the user interface, or later feedback based on Web-based data viewing, or via methods that include summary reports provided on a regular schedule (e.g., a daily schedule).

The exercise cycle 210 is designed for structural robustness, low cost, and convenient deployment in a clinic bed or operating as a floor mounted device. In some embodiments, proper enclosure and additional metal support are added to the exercise cycle 210 for both mechanical stability and sensor instrumentation. In some embodiments, the exercise cycle 210 comprises a base stand 260 for aiding in stabilization of the exercise cycle 210. Preferably, the crank 220 and the resistance hub 230 are coupled to the base stand 260. In some embodiments, the base stand 260 comprises two legs 265, preferably disposed on opposite sides of the stand 260. However, it is contemplated that other configurations are within the scope of the present invention.

Regarding sensor instrumentation, both force and Hall-effect sensors are inexpensive and can be deployed directly. In some embodiments, the sensing platform (e.g., MicroLEAP) is mounted inside tubing of the exercise cycle 210 near an end in order to maintain maximum wireless signal strength. However, it is contemplated that other configurations are within the scope of the present invention.

In some embodiments, cadence, or rotational speed, is measured by introducing a fixed sampling location along the trajectory of the crank 220. Every time the crank 220 passes the sampling location, the sensing unit of the exercise cycle 210 registers a trigger. In some embodiments, cadence is computed by measuring time difference between two successive triggers. In some embodiments, the fixed sampling location is instrumented with a sensor 250, such as a Hall-effect sensor (e.g., the Honeywell SS49E), located on one side of the resistance hub 230, as seen in FIG. 2B. In some embodiments, a small magnet 255 is attached to the same side of the crank 220, as seen in FIGS. 2B-C. As the magnet 255 travels over the sensor 250 via the crank 220, the sensor 250 detects the corresponding magnetic field and produces an analog voltage proportional to the strength of the field. By computing the time difference, $\Delta t$, between two consecutive voltage peaks, the exercise system of the present invention can compute the cadence and corresponding angular frequency, $\omega$, of the cycle:

$$\text{cadence [rpm]} = \frac{\Delta t}{f_{sampling}} \cdot (60 \text{ s}) \quad (1)$$

$$\omega[\text{rad/s}] = \frac{2\pi \cdot 60 \text{ s}}{\text{cadence [rpm]}} \quad (2)$$

where $f_{sampling}$ corresponds to the sampling frequency of the sensing platform.

In some embodiments, measurement of torque, power, and energy requires measurement of the force exerted on the crank and its rotational speed. In some embodiments, the sensing unit on the exercise cycle 210 measures the torque by measuring the force exerted by the tab 235 under the resistance hub 230. In some embodiments, both the crank 220 and the tab 235 are connected to a single rigid resistance hub 230, so force exerted on the crank 220 is measured by the force produced by the tab 235. In some embodiments, a thin-film polymer force sensor is applied for measurement of force at the tab. It has been found that the use of TekScan's Flexiforce sensor is particularly useful in the present invention due to its availability and high repeatability. This sensor system exhibits both large resistance and large response to force. In some embodiments, the sensing unit uses a polymer conductive strain sensor due to its low cost and large resistance response to strain. This large response enables the implementation of analog microelectronic measurement interfaces at low cost in comparison to alternative conventional solutions based on the conventional metal strain gage.

In some embodiments, torque measurement at time t, $\tau(t)$, requires the knowledge of the applied force, F(t), and the radial length (displacement vector), r(t). In some embodiments, when the tab applies force to the force sensor, the conductance of the sensor changes proportionally.

Figure 2D:
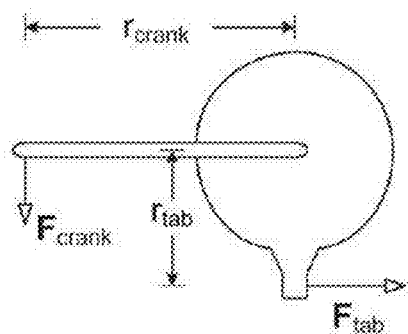
FIG. 2D illustrates a side view of a torque measurement system for an exercise cycle in accordance with some embodiments of the present invention.

Consider FIG. 2D: a net force, $F_{crank}(t)$, is exerted on the resistance hub. Now, $\|\tau(t)\| = \|r(t) \times F(t)\|$, where × denotes the cross product. The welded tab 235 and the crank 220 are connected to the same resistance hub, and thus net torque must remain the same:

$$\tau_{crank} = \tau_{tab} \quad (3)$$

Figure 2E:
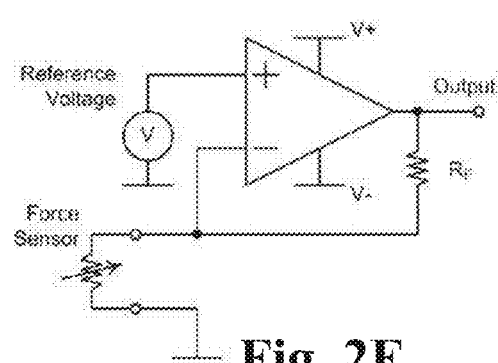
FIG. 2E illustrates a parametric circuit for an exercise cycle in accordance with some embodiments of the present invention.

The parametric circuit in FIG. 2E converts the conductance generated by $\|\tau_{tab}\|$ an output voltage:

$$V_{out} = V_{ref}(1 + R_f G) \quad (4)$$

where G is the conductance of the force sensor.

In some embodiments, the average power, $P_{avg}$, is defined as the average of the product of angular frequency and torque over a time duration T:

$$P_{avg} = \frac{1}{T} \int_0^T \|\tau(t)\| \cdot \omega(t) \, dt \quad (5)$$

Equation (3) describes the translation of the external force applied on the resistance hub to a corresponding force applied on force sensor. In some embodiments, both the force and resulting conductance of the force sensor used in the sensing unit exhibit a linear relationship:

$$G = \alpha \cdot F \quad (6)$$

where $\alpha$ is the proportionality constant determined empirically.

In some embodiments, by design, $\theta_{tab}$ is close to 90 degrees at all times. Equation (3) enables computation of external torque by measuring $\|F_{tab}\|$. All of $\|F_{tab}\|$ appears on the force sensor. Substituting Equations (3), (4) and (6) yields the relationship:

$$V = m \cdot F_{tab} + c = \left(\alpha R_f V_{ref} \frac{r_{crank}}{r_{tab}}\right) \cdot F_{tab} + V_{ref} \quad (7)$$

Equations (7) and (8) provide a method for in situ calibration: Place a minimum of two known weights on the resistance hub ($F_{tab}$) and record the resulting voltages ($V_{ref}$). Because the relationship is linear, one can estimate m and c by using a linear best-fitting curve. The estimated slope and offset from the calibration should match up closely to the predicted slope and offset:

$$m = \alpha R_f V_{ref} \frac{r_{crank}}{r_{tab}} \quad (8)$$

$$c = V_{ref} \quad (9)$$

It is contemplated that the computations and determinations of crank measurements discussed above (e.g., cadence, torque, and power) can be performed by the sensing unit on the exercise cycle 210 or on a remote device, such as a mobile device or a remote host.

Figure 3:
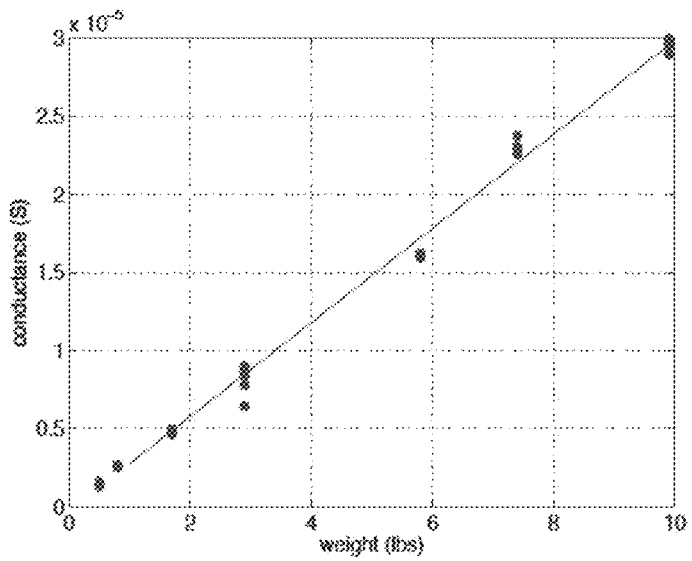
FIG. 3 is a graph illustrating a sample calibration of force sensors in accordance with some embodiments of the present invention.

FIG. 3 shows a sample calibration of force sensors using three different weights, with the conductance of the sensor being plotted in relationship to different weights. As expected, the empirical calibration function closely matches up with the expected function.

Figure 4:
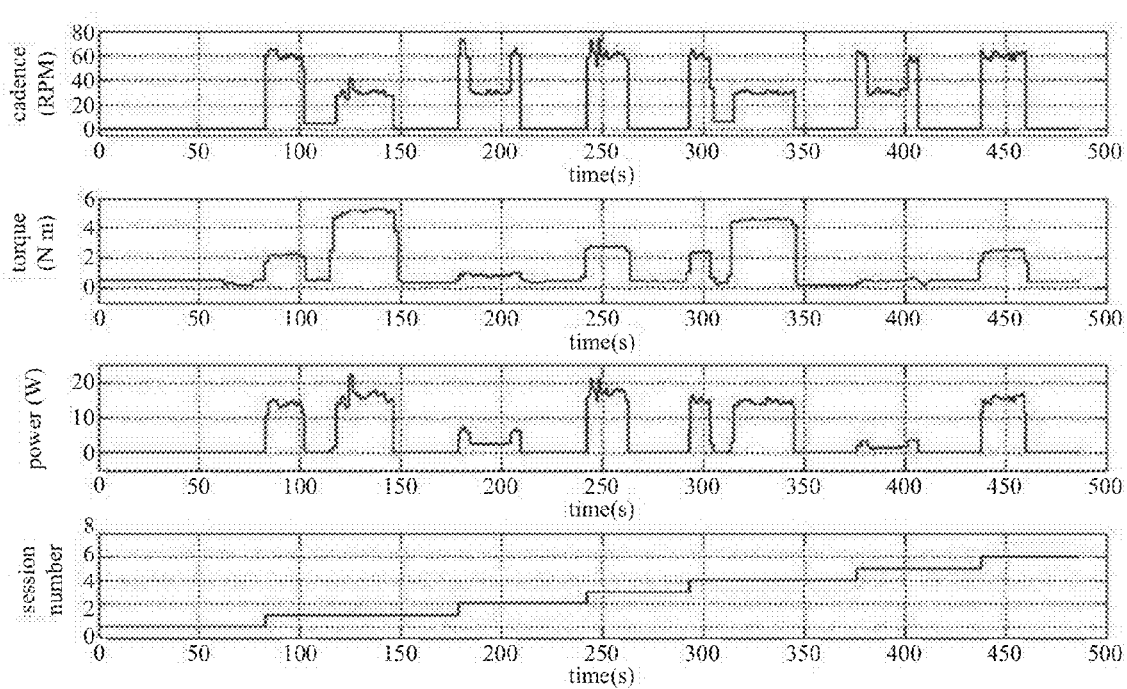
FIG. 4 is a graph illustrating a test experiment for varying sensor data along with computed power and recorded sessions in accordance with some embodiments of the present invention.

FIG. 4 illustrates a test experiment for varying cadence and resistance values. The cadence-time characteristic captures the speed in a cycle-by-cycle fashion. As a result, the cadence-time characteristic exhibits a step-wise waveform. Similarly, FIG. 4 shows a torque-time characteristic, a power-time characteristic, and a session-number-time characteristic. When the sensing unit does not detect a new trigger from the sensor within a certain time limit, it assumes the present session has concluded. The next trigger automatically indicates the beginning of a new session. The time limit can be set by a subject user or caregiver for automatically computing the number of sessions completed by the patient. In FIG. 4, the time limit is 20 seconds. Therefore, the sensing unit infers that there are 6 episodes, as reflected by the session-number-time characteristic.

In some embodiments, resistances are monitored and reported as continuous values or divided into levels that may denote standard values of: low, medium, and high. In some embodiments, the resistance knob 240 on the exercise cycle 210 controls the pedal force resistance that the patient experiences, and the torque-time characteristic illustrates the generated torque resulting from this setting and the user applied force. In some embodiments, the measured torque exhibits a non-zero offset value for zero applied torque. This is recorded and removed in the data processing. The power-time characteristic is the product of the speed and torque values. Finally, energy developed by a subject over a session of usage is the time integral of generated power. It is contemplated that these analyses, computations, and inferences discussed above with respect to FIG. 4 can be performed by the sensing unit on the exercise cycle or by a remote device, such as a mobile device or a remote host.

In some embodiments, the present invention provides a user interface on a remote device, preferably a mobile device.

Figure 5A:
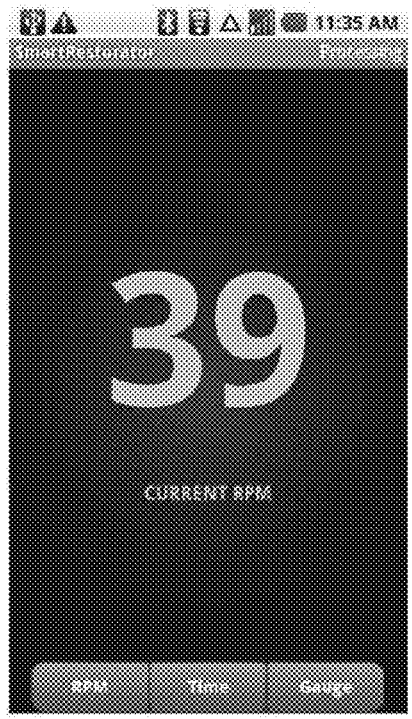
FIG. 5A illustrates a user interface that shows the real-time display of cadence in accordance with some embodiments of the present invention.

The user interface is configured to display information related to a patient's use of the exercise cycle (i.e., rotation of the crank). Such information includes, but is not limited to, cadence, torque, power, and number of sessions. In some embodiments, this information is updated on a cycle-to-cycle basis. In some embodiments, the user interface employs an Android-based operating system. However, it is contemplated that the use of other operating systems are within the scope of the present invention. FIG. 5A shows the real-time display of cadence (RPM) while the patient is using the exercise cycle.

Figure 5B:
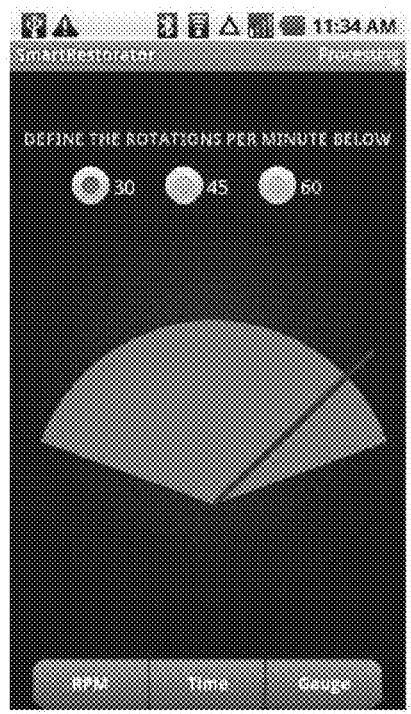
FIG. 5B illustrates a user interface that shows a patient's adherence to a desired cadence in accordance with some embodiments of the present invention.

In some embodiments, the user interface is also configured to show the patient's performance in relation to a certain standard. For example, in some embodiments, the user interface enables a user to set a desired cadence or torque or power using the user interface, and then displays the user's performance in relation to this desired measurement, such as how close the user is to the desired measurement or whether the user has met, exceeded, or fell short of the desired measurement. FIG. 5B shows a patient's adherence to a 30 rotations-per-minute standard. In particular, the needle in the gauge indicates if the patient is adhering to the desired cadence (needle in the center), performing too slow (needle to the left), or performing too fast (needle to the right). In FIG. 5B, since the user's cadence is at 39 RPM, the patient is exceeding the 30 rotations-per-minute desired cadence, and thus the needle is positioned on the right portion of the gauge.

Figure 6A:
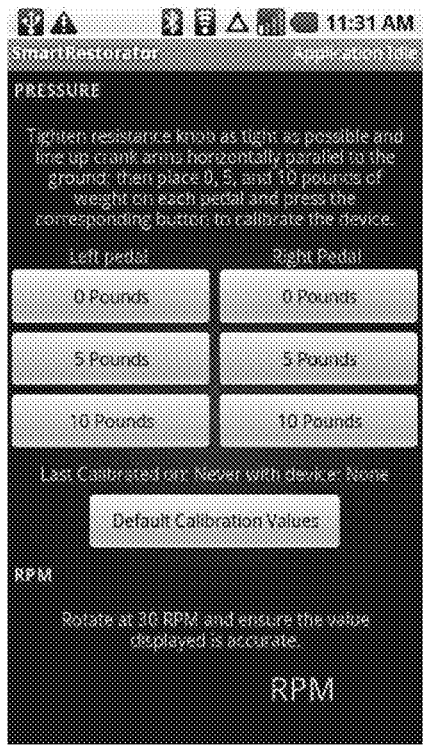
FIG. 6A illustrates a user interface that supports calibration of the exercise system in accordance with some embodiments of the present invention.
Figure 6B:
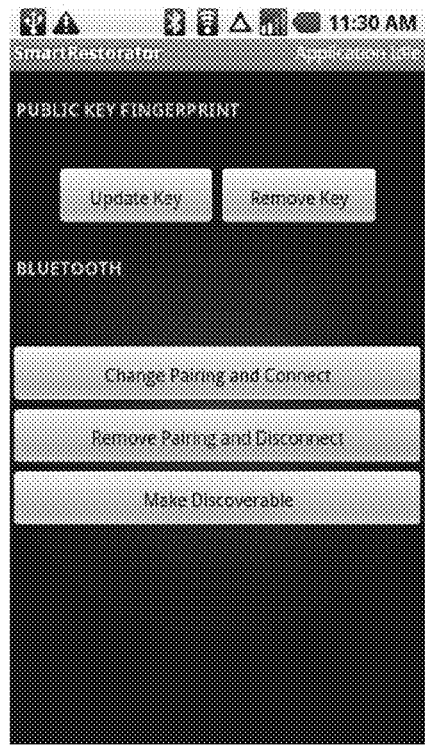
FIG. 6B illustrates a user interface that supports configuration of the exercise system in accordance with some embodiments of the present invention.

In some embodiments, the user interface enables a user to calibrate and configure a remote device with the exercise cycle. FIGS. 6A-B show interfaces that support calibration and configuration of the discovery and authentication that pairs a handheld device with the exercise cycle of the present invention. In FIG. 6A, the user interface provides instructions to the user for calibrating the system with different weights. The user places a certain weight on each pedal of the exercise cycle, and then activates a corresponding button displayed on the handheld device. This step can be repeated for different weights until proper calibration is achieved. In some embodiments, the user interface provides the user with the option of selecting default calibration values. In FIG. 6B, the user interface provides the user with options related to authenticating the handheld device and the exercise cycle.

Figure 7:
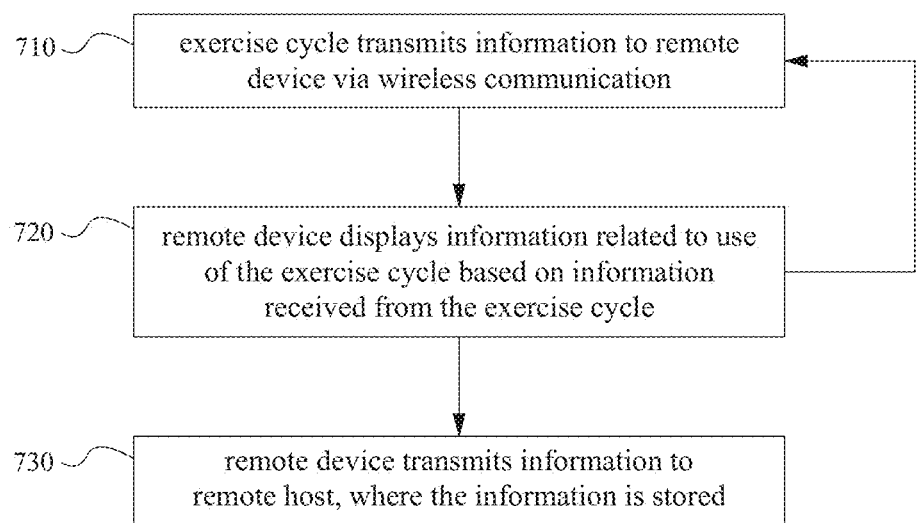
FIG. 7 is a flow chart illustrating a method of monitoring exercise in accordance with some embodiments of the present invention.

FIG. 7 is a flow chart illustrating a method of monitoring exercise in accordance with some embodiments of the present invention. At step 710, a user rotates the crank of an exercise cycle, such as exercise cycle 210 discussed above, and the exercise cycle transmits information to a remote device via wireless communication, such as Bluetooth. In some embodiments, the remote device is a mobile device, such as a mobile phone. The transmitted information s related to at least one crank measurement. Such information can include, but is not limited to, voltage and/or time measurements obtained by the sensing unit of the exercise cycle. Such information can also include more advanced information, including, but not limited to, cadence, torque, power, energy, and session numbers. At step 720, the remote device displays information related to use of the exercise cycle based on the information received from the exercise cycle. Such displayed information can include, but is not limited to, any of the information discussed above with respect to FIGS. 5A-B. The method repeats until the user stops using the exercise cycle for a certain amount of time. In some embodiments, at step 730, the remote device transmits information to a remote host, such as a medical database, where the information is stored. This transmitted information is related to the user's use of the exercise cycle and can comprise any of the previously discussed information (i.e., cadence, torque, etc.). Preferably, the information stored in the remote host is accessible to users, such as patients, caregivers, nurses, and physicians.

The present invention provides a sensor-equipped portable exercise cycle developed to provide a low cost, rapidly-deployable, and remotely-monitored system for promoting general wellness and exercise-prescribed treatment, including rehabilitation. It measures cadence, torque, and power, the critical parameters for evaluating a patient's progress. The present invention provides a cost-effective solution by providing a real-time sensing and monitoring capability through a selection of sensor technology that is inherently low cost. The exercise cycle is preferably portable allowing caregivers and the clinic to monitor and deploy this system both during and after a hospital stay, and in residential, assisted living, and nursing home environments. The present invention's sensing systems are available for local handheld devices providing guidance, display devices integrated into the exercise cycle, and remote monitoring, data processing, archiving, and data display via remote Web services.

The present invention provides a portable, cost-effective solution for physical rehabilitation. By incorporating wireless sensing technology into an exercise cycle, along with data transport and data archiving, patients, caregivers, nurses, and physicians can analyze the progress of patient activity and rehabilitation in real time. The graphic user interface also provides a method for motivating patients to adhere to their regimented exercise routines and tracking their daily progress.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications can be made in the embodiment chosen for illustration without departing from the spirit and scope of the invention as defined by the claims.

What is claimed is:

1. An exercise system comprising:
   an exercise cycle comprising a crank, wherein the crank is configured to be rotated by a user; and
   a sensing unit coupled to the exercise cycle, wherein the sensing unit is configured to sense information related to at least one crank measurement and to transmit the information related to the at least one crank measurement to a remote device via wireless communication, wherein the at least one crank measurement comprises the force applied to the crank, wherein the exercise cycle further comprises a resistance hub and a tab coupled to the resistance hub, wherein the crank is configured to translate the force that is applied to it to the tab, and the tab is configured to apply the force that is applied to it to the sensing unit.

2. The exercise system of claim 1, wherein the remote device is a mobile device.

3. The exercise system of claim 1, wherein the at least one crank measurement comprises a rotational speed of the crank or a force applied to the crank.

4. The exercise system of claim 1, wherein the remote device is configured to determine the at least one crank measurement using the transmitted information.

5. The exercise system of claim 1, wherein:
   the exercise cycle further comprises a resistance hub; and
   the crank comprises a first arm and a second arm, the first arm extending from a first side of the resistance hub and terminating in a first end, and the second arm extending from a second side of the resistance hub opposite the first side and terminating in a second end.

6. The exercise system of claim 5, wherein a first pedal is coupled to the first arm at the first end, and a second pedal is coupled to the second arm at the second end.

7. The exercise system of claim 1, wherein the at least one crank measurement comprises a rotational speed of the crank.

8. The exercise system of claim 7, wherein the sensing unit is configured to register a trigger event when the crank passes a sampling location.

9. The exercise system of claim 8, wherein the sensing unit is configured to measure the rotational speed of the crank by measuring the time between successive trigger events or to register the trigger event with a remote device that is configured to measure the rotational speed of the crank by measuring the time between successive trigger events.

10. The exercise system of claim 7, wherein:
a magnet is coupled to the crank, wherein the magnet produces a magnetic field having a magnitude; and
the sensing unit is configured to detect the magnetic field and to produce a voltage that is proportional to the magnitude of the magnetic field.

11. The exercise system of claim 10, wherein the sensing unit comprises a Hall-effect sensor.

12. The exercise system of claim 10, wherein the sensing unit is configured to measure the rotational speed of the crank by measuring the time between successive voltage peaks or to communicate the produced voltage to a remote device that is configured to measure the rotational speed of the crank by measuring the time between successive voltage peaks.

13. The exercise system of claim 1, wherein the sensing unit is configured to measure torque of the crank using the applied force measurement or to communicate the applied force to a remote device that is configured to measure torque of the crank using the applied force measurement.

14. The exercise system of claim 1, wherein the sensing unit comprises a polymer force sensor.

15. The exercise system of claim 1, wherein the sensing unit comprises a polymer conductive strain sensor.

16. The exercise system of claim 1, wherein the sensing unit is configured to be used to determine the rotational speed of the crank and the force applied to the crank.

17. The exercise system of claim 16, wherein:
the sensing unit is configured to determine the rotational speed of the crank or to transmit information related to the rotational speed of the crank to a remote device that is configured to determine the rotational speed of the crank using the transmitted information related to the rotational speed of the crank; and
the sensing unit is configured to determine the torque of the crank or to transmit information related to the force applied to the crank to a remote device that is configured to determine the torque of the crank using the transmitted information related to the force applied to the crank.

18. The exercise system of claim 1, wherein the exercise cycle further comprises a resistance hub and a resistance control knob coupled to the resistance hub, wherein the resistance control knob is configured to control an amount of resistance to movement of the crank.

19. The exercise system of claim 18, further comprising plastic friction pads configured to sandwich a portion of the crank with a clamping force, wherein the resistance control knob is configured to adjust the clamping force.

* * * * *